(12) United States Patent
Silveri et al.

(10) Patent No.: US 11,460,432 B1
(45) Date of Patent: Oct. 4, 2022

(54) EXTENDED LIFE ELECTRODE MEASUREMENT METHOD AND APPARATUS

(71) Applicant: Halogen Systems, Inc., Incline Village, NV (US)

(72) Inventors: Michael A. Silveri, Incline Village, NV (US); Adam Moore, Reno, NV (US)

(73) Assignee: Halogen Systems, Inc., Reno, NV (US)

( * ) Notice: Subject to any disclaimer, the term of this patent is extended or adjusted under 35 U.S.C. 154(b) by 118 days.

(21) Appl. No.: 17/014,632

(22) Filed: Sep. 8, 2020

(51) Int. Cl.
*G01N 27/416* (2006.01)
*G01N 27/403* (2006.01)
*G01N 27/327* (2006.01)

(52) U.S. Cl.
CPC ....... *G01N 27/403* (2013.01); *G01N 27/3273* (2013.01); *G01N 27/4161* (2013.01)

(58) Field of Classification Search
CPC ............. G01N 27/403; G01N 27/3273; G01N 27/4161; G01N 27/327; G01N 27/4163; G01N 27/38
See application file for complete search history.

(56) References Cited

U.S. PATENT DOCUMENTS

| | | | |
|---|---|---|---|
| 6,238,555 B1 | 5/2001 | Silveri et al. | |
| 6,270,680 B1 | 8/2001 | Silveri et al. | |
| 7,566,392 B2 * | 7/2009 | Cheng | G01N 27/49 204/402 |
| 7,767,067 B2 | 8/2010 | Silveri | |
| 8,298,391 B2 | 10/2012 | Silveri | |
| 8,887,556 B2 | 11/2014 | Silveri | |
| 9,664,636 B2 * | 5/2017 | Wen | G01N 27/4045 |

OTHER PUBLICATIONS

LaCourse, William R., "Pulsed Amperometric Detection in HPLC," Pulsed Electrochemical Detection in High-Performance Liquid Chromatography, Wiley-Interscience, 1st Edition, Aug. 18, 1997, Chapter 4, pp. 86-121.

* cited by examiner

*Primary Examiner* — Alexander S Noguerola
(74) *Attorney, Agent, or Firm* — Patterson Intellectual Property Law, P.C.; Jerry Turner Sewell

(57) ABSTRACT

A method and apparatus extend the measurement life of a working electrode in a three-electrode amperometric sensor by applying an activation sequence of voltages and a measurement sequence of voltages to the input of a potentiostat. The activation sequence includes multiple cycles wherein each cycle includes a low (more negative) voltage and a high (more positive) voltage (e.g., 0 volts) with reference to a signal ground reference. In one mode, the measurement sequence includes multiple cycles of three voltage pulses, wherein each cycle includes a measurement voltage pulse followed by a high (more positive) pulse, followed by a low (more negative) pulse. The cycles are repeated N times. In a second mode, the measurement sequence comprises a fixed measurement voltage having selectable duration.

14 Claims, 3 Drawing Sheets

EXTENDED LIFE ELECTRODE MEASUREMENT METHOD AND APPARATUS

BACKGROUND

Amperometric sensors have been used for more than forty years for measurement of chlorine concentration in drinking water and wastewater. A few variations have occurred over the years, but the basic technology has not changed much. When chlorine is added to water in any form, the following reaction in Equation (1) occurs:

$$Cl_2 + H_2O \rightleftharpoons HOCl + H^+ + Cl^- \quad (1)$$

The reaction at the working electrode (cathode) in an amperometric sensor is a reduction of the chlorine to chloride in accordance with the following Equation (2):

$$HOCl + H^+ + 2e \rightarrow Cl^- + H_2O \quad (2)$$

The liberated electrons caused by the reduction are measured (in nanoamperes) and are directly proportional to the concentration of chlorine in solution.

FIG. 1 illustrates an embodiment of a typical potentiostat 100 for measuring chlorine concentration in accordance with the foregoing equations. The potentiostat includes a measurement cell 110 that includes a working electrode (WE) 112, a reference electrode (RE) 114 and a counter (or auxiliary) electrode (CE) 116. In the illustrated embodiment, the working electrode is a bare electrode comprising gold.

The working electrode 112 is coupled to a signal ground (S_GND) reference 120 via a current sensing resistor 122, which is a resistor having a very low resistance (e.g., 0.1 ohm or less). The signal ground reference may be a conventional circuit ground reference at zero volts or may be an offset voltage reference. For example, in the illustrated potentiostat having circuits connected to a single 5-volt power supply, the signal ground reference may be set at approximately one-half the supply voltage (e.g., approximately 2.5 volts). In other embodiments having components connected between a positive supply voltage and a negative supply voltage, the signal ground reference is also the circuit ground reference. In the following description directed to the illustrated embodiment, a reference to 0 volts is a reference to the signal ground reference. The other signal voltages discussed herein and in the claims are positive (greater than) or negative (less than) with respect to the signal ground reference.

An output of a driving amplifier 130 is coupled to the counter electrode 116. The driving amplifier drives the counter electrode to a voltage with respect to the working electrode to allow a current to flow between the working electrode 112 and the counter electrode. The current flowing through the measurement cell causes a reference voltage to develop on the reference electrode 114 with respect to the working electrode responsive to the magnitude of the current. An output amplifier 140 buffers the reference voltage and provides a buffered reference voltage corresponding to the magnitude of the reference voltage to a summing node 144 via a first summing node resistor 142. An input voltage ($V_{IN}$) is buffered by an input amplifier 150 to provide a buffered input voltage. The buffered input voltage is provided to the summing node via a second summing node resistor 152. A summed voltage on the summing node voltage is responsive to a difference between the buffered reference voltage and the buffered input voltage.

The summed voltage on the summing node 144 is coupled to an inverting (−) input of the driving amplifier 130. A noninverting (+) input of the driving amplifier is coupled to the signal ground reference 120. The driving amplifier is responsive to the summed voltage on the summing node to vary the output voltage applied to the counter electrode 116 until the measured voltage on the reference electrode 114 is substantially equal to the input voltage to cause the summed voltage on the inverting input to be substantially equal to the voltage of the signal ground reference. The potentiostat operates in a known manner to maintain the applied voltage on the working electrode 112 versus the reference electrode equal to the input voltage $V_{IN}$ by varying the current through the counter electrode. The magnitude of the current ($I_{CELL}$) flowing through the cell from the working electrode to the counter electrode is measured by sensing a voltage across the voltage sensing resistor 122. The magnitude of the current is determined by the electrons released by reducing hypochlorous acid (HOCl) at the working electrode in accordance with Equation (2). The current is proportional to the reduction and thus proportional to the concentration of chlorine in the water.

A common problem encountered with online measurement of water chemistry in the field using a typical potentiostat is fouled electrodes in the sensor system. Electrode measurements can be rendered unreliable when the working electrode is covered with inorganic (salts such as calcium carbonate) layers or with organic (biofouling) layers that inhibit electrode processes. Compounds may also be adsorbed onto the metal electrode surface resulting in passivation of the electrode surface. An electrode surface changes as a function of time and exposure, which will change (increase or decrease) the sensitivity of the potentiostat to chlorine or other oxidants. These changes result in a loss of calibration.

Electrodes can also suffer a delay in stabilizing when first put into service. Polarization of many sensors causes a loss of sensitivity over the first 2-24 hours, requiring recalibration. Sensitivity is also reduced and the calibration changes if the sensor is removed and replaced. This was largely overcome in prior patents that use a negative potential of −2.0 V for 1 to 5 seconds. All potentials noted are versus an Ag/AgCl reference electrode.

One current amperometric measurement system uses a stabilization pulse of −2.0 V for 1 to 5 seconds. The stabilization pulse prevents polarization and improves the repeatability of the measurement. While this method provides substantial improvements to an amperometric measurement system, some variations still occur from one measurement to the next.

Activation sequences are well known in amperometry. In a first step, hydrogen evolves at the working electrode (WE) at a potential of −2 volts with respect to the reference electrode (RE). This is followed by another step of at a potential of 0 volts (e.g., the voltage on the signal ground reference). In certain known systems, each step requires at least 10 seconds. This activation sequence is repeated ten or more times and has the effect of cleaning the electrode and activating the electrochemical surface. These techniques are widely used in laboratories working with electrochemical detectors. These techniques are often used after polishing the electrode to restore or activate the electrochemical surface to improve detection and waveform definition in cyclic voltammetry. These techniques are not practical for online instruments.

A disadvantage of the known technique lies in the number of normal measurement cycles that must be performed before the electrode sensitivity is restored and stable. For example, one known system requires 3 to 5 cycles before electrode sensitivity is restored and stable. This is a very long time when near real-time measurements are required. If ten cycles with two steps of ten seconds are used and repeated at least 10 times (more than 10 repetitions are often required), this activation sequence takes at least 200 seconds. If the normal measurement cycle is 40 seconds and must be repeated 3 to 5 times, the elapsed time may be as much as 400 seconds or almost 7 minutes during which no measurement is possible. This downtime in an online process control system is unacceptable and cannot practically be performed every cycle.

Another problem with amperometric measurements occurs in seawater measurements of chlorine (total residual oxidant ((TRO)). Gold working electrodes can be used for high signal sensitivity of TRO. However, the combination of high levels of chlorine in seawater can degrade the signal due to a loss of gold from the surface of the electrode.

SUMMARY

An object of the system and method disclosed herein is to improve the stability of online amperometric measurements made by a process instrument by using an activation sequence to prepare a stable electrochemical surface prior to and after each measurement without unduly increasing the length of the measurement cycle to improve precision in measurements.

An object of the system and method disclosed herein is to enable a long-life electrode in any salinity from freshwater to seawater, to minimize the potential for fouling of the electrodes, and to rapidly stabilize the measurement after applying cleaning waveforms.

One aspect of the embodiments disclosed herein is a method and apparatus to extend the measurement life of a working electrode in a three-electrode amperometric sensor. The method and apparatus apply an activation sequence of voltages and a measurement sequence of voltages to the input of a potentiostat. The activation sequence includes multiple cycles wherein each cycle includes a low (more negative) voltage and a high (more positive) voltage (e.g., 0 volts). In one mode, the measurement sequence includes multiple cycles of three voltage pulses, wherein each cycle includes a measurement voltage pulse followed by a high (more positive) pulse, followed by a low (more negative) pulse. The cycles are repeated N times. In a second mode, the measurement sequence comprises a fixed measurement voltage having selectable duration.

Another aspect in accordance with the embodiments disclosed herein is a method for extending the measurement life of a working electrode in a three-electrode amperometric sensor for online measurement of a water parameter. The amperometric sensor includes a potentiostat with selectable voltages. The working electrode is a bare electrode. The method comprises selectively switching between a first mode and a second mode, each mode including an activation step followed by a measurement step. The activation step comprises applying a first set of voltages to the working electrode. The first set of voltages comprises a plurality of cycles that switch from a more negative voltage in a range of −1 volt to −2.5 volts to a more positive voltage in a range of −0.2 volt to +0.5 volt. The plurality of cycles range from 10 cycles to 100 cycles. In the first mode, the measurement step comprises applying a pulsed amperometric detection (PAD) sequence of three voltages to measure a current corresponding to a level of a water parameter. The sequence of three voltages comprises a first voltage in a range of −0.1 volt to +0.3 volt having a duration in a range of approximately 300 milliseconds to approximately 500 milliseconds; a second voltage in a range of 0.65 volt to 0.95 volt having a duration in a range of 20 milliseconds to 300 milliseconds; and a third voltage in a range of −1.0 volt to −2.5 volts having a duration in a range of 20 to 300 milliseconds. The method further comprises measuring a sensor current through the sensor while the first voltage in the sequence of three voltages is applied. The sequence of three voltages is repeated for at least 10 times and the sensor currents are averaged to derive a current for parameter calculation. In the second mode, the measurement step comprises switching from the PAD sequence of three voltages to a fixed measurement potential to measure the current when the measured current is below a selected signal current value. The fixed measurement potential has a range from −0.05 volt to 0.5 volt and has a duration in a range from 3 seconds to 60 seconds.

In certain embodiments in accordance with this aspect, switching occurs when the selected signal current level is below 50,000 nanoamperes. In certain embodiments in accordance with this aspect, switching occurs when the selected signal current level is below 5,000 nanoamperes. In certain embodiments in accordance with this aspect, switching occurs when the selected signal current level is below 500 nanoamperes. In certain embodiments in accordance with this aspect, the duration is 20 seconds and the measurement potential is 0.0 volts.

In certain embodiments in accordance with this aspect, the working electrode comprises gold.

In certain embodiments in accordance with this aspect, the cycles in the first set of voltages switch from −1.5 volts to 0.0 volts, and the plurality of cycles comprises 20 to 40 cycles. In certain embodiments in accordance with this aspect, the cycles in the first set of cycles switch from −1.5 volts to 0.0 volts, and the plurality of cycles comprises 30 cycles. In certain embodiments in accordance with this aspect, the first voltage in the sequence of three voltages is 0.0 volts, the second voltage in the sequence of three voltages is 0.8 volt and the third voltage in the sequence of three voltages is −1.15 volts. In certain embodiments in accordance with this aspect, the sequence of three voltages is repeated up to 40 times.

Another aspect in accordance with the embodiments disclosed herein is an apparatus for measuring a water parameter. The apparatus comprises a three-electrode potentiostat, which comprises a measurement cell having a working electrode, a reference electrode and a counter electrode. The potentiostat further includes circuitry responsive to an input voltage to generate a current through the measurement cell to cause a voltage between the working electrode and the reference electrode responsive to the input voltage. A waveform generator has an output coupled to the potentiostat. The waveform generator generates the input voltage. The waveform generator operates in at least a first mode and a second mode. In the first mode, the waveform generator generates the input voltage as an activation sequence followed by a first measurement sequence. The input voltage in the activation sequence comprises a first set of voltages in a plurality of cycles that switch from a more negative voltage in a range of −1 volt to −2.5 volts to a more positive voltage in a range of −0.2 volt to +0.5 volt. The plurality of cycles in the activation sequence range from 10 cycles to 100 cycles. The input voltage in the measurement sequence comprises a repeated sequence of three voltages comprising a first voltage in a range of −0.1 volt to +0.3 volt having a duration in a range of approximately 300 milliseconds to approximately 500 milliseconds; a second voltage in a range of 0.65 volt to 0.95 volt having a duration in a range of 20 milliseconds to 300 milliseconds; and a third voltage in a range of −1.0 volt to −2.5 volts having a duration in a range of 20 to 300 milliseconds. In the second mode, the waveform generator generates the input voltage as the activation sequence followed by a second measurement sequence. The second measurement sequence comprises a fixed measurement voltage. The fixed measurement voltage has a range from −0.05 volt to 0.5 volt and has a duration in a range from 3 seconds to 60 seconds. A current sensor senses the current flowing through the measurement cell as a measured current.

In certain embodiments in accordance with this aspect, the waveform generator repeats the sequence of three voltages at least 10 times, and the measured currents are averaged to derive a current for a water parameter calculation.

In certain embodiments in accordance with this aspect, the working electrode comprises gold.

BRIEF DESCRIPTIONS OF THE DRAWINGS

DETAIL DESCRIPTION

Figure 1:
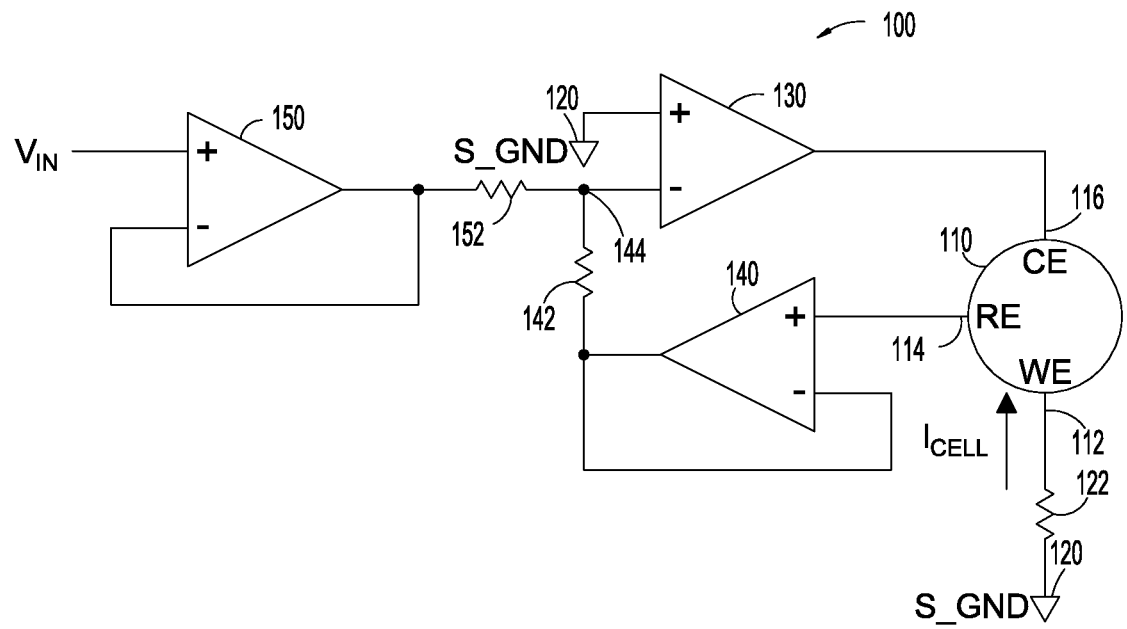
FIG. 1 illustrates a typical potentiostat configuration using buffers to isolate a driving amplifier and a reference electrode.
Figure 2:
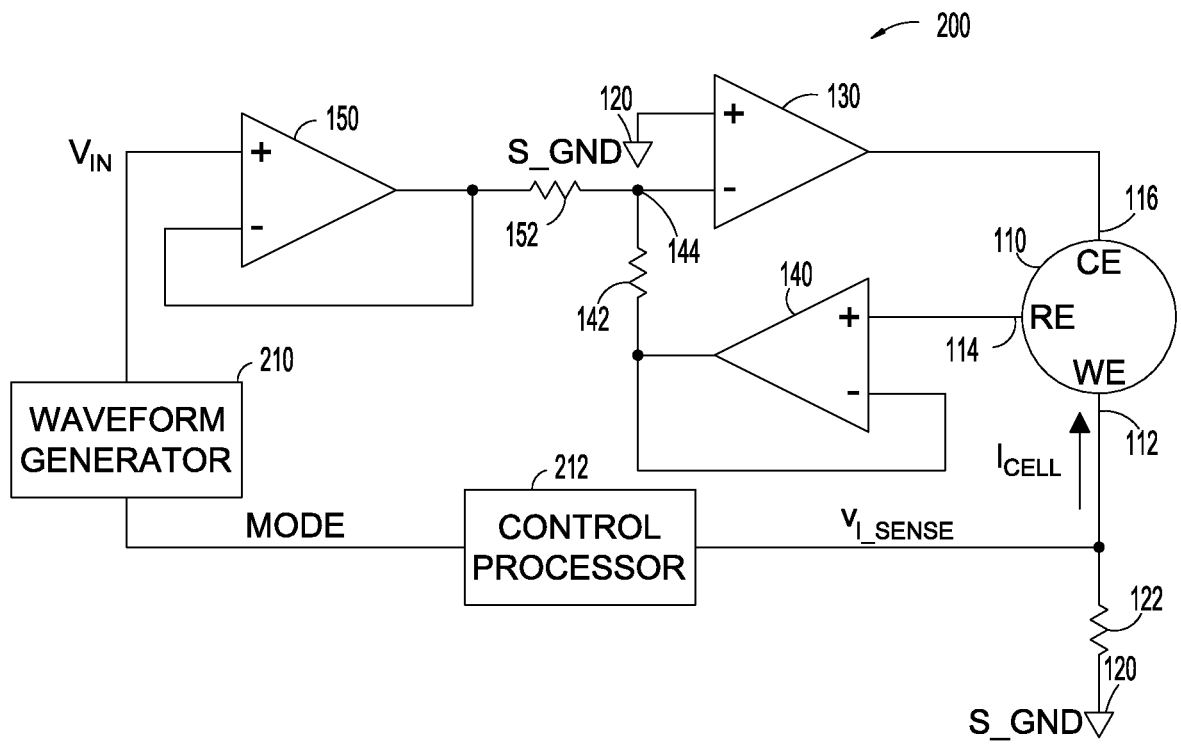
FIG. 2 illustrates a potentiostat configuration having a waveform generator that provides a sequence of voltage potentials to the input amplifier of the potentiostat.

The system and method disclosed herein use an activation method to provide rapid electrode cleaning and a pulse-switch method to maximize electrode life and minimize the need for electrode recalibration. FIG. 2 illustrates an improved potentiostat 200 corresponding in part to the potentiostat 100 of FIG. 1. In addition to the elements of the previously described potentiostat, the improved potentiostat includes a waveform generator 210 that generates waveforms that are applied as the input voltage ($V_{IN}$) to the input of the input amplifier 150 of the potentiostat. The waveform generator may comprise a microprocessor, a field programmable gate array (FPGA), a custom application specific integrated circuit (ASIC), a plurality of logic circuits or the like that produce the waveforms described below. The waveform generator is responsive to a mode (MODE) signal from a control processor 212 to switch between at least a first mode and a second mode. The control processor receives a sensed voltage ($V_{I\_SENSE}$) generated across the sensing resistor 122. The sensed voltage is proportional to the current ICELL through the measurement cell 110. In the first mode, the waveform generator generates a first waveform 220 illustrated in FIG. 3. The waveform generator can be switched to a second mode in which the waveform generator generates a second waveform 230 illustrated in FIG. 4. Each waveform comprises an activation sequence 250 followed by a respective measurement sequence as described below. In the first waveform 220 of FIG. 3, the measurement sequence is a pulsed amperometric detection (PAD) sequence 260. In the second waveform 230 of FIG. 4, the measurement sequence is a constant fixed potential sequence 270. Both sequences are described below. The selected waveform from the waveform generator 210 is applied to the input of the driving amplifier 130 in the potentiostat 200. The potentiostat operates as described above, to maintain the voltage between the working electrode 112 and the reference electrode 114 equal to the applied input voltage VIN generated by the waveform generator. Accordingly, the voltage between the working electrode and the reference electrode varies with the input voltage.

Figure 3:
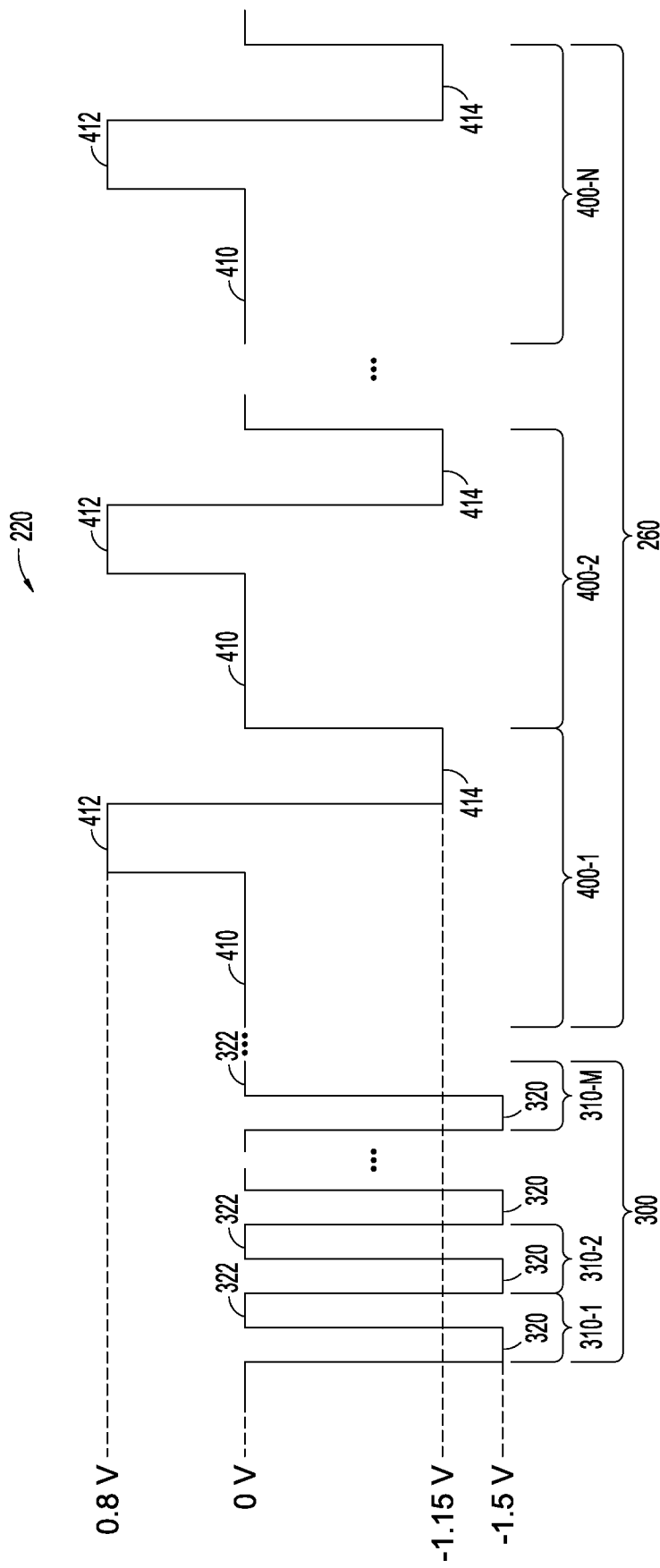
FIG. 3 illustrates a waveform generated by the waveform generator of FIG. 2 comprising an activation sequence followed by a pulsed amperometric detection (PAD) sequence.
Figure 4:
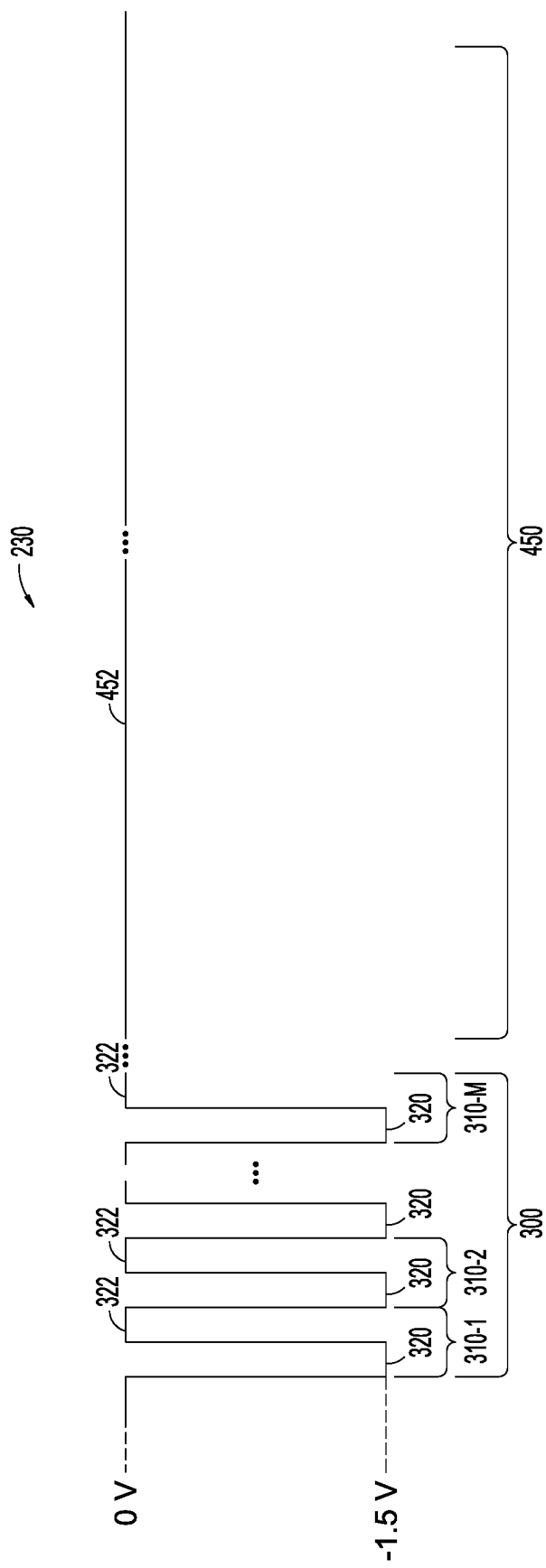
FIG. 4 illustrates a waveform generated by the waveform generator of FIG. 2 comprising an activation sequence followed by a fixed measurement duration.

Each of the first waveform 220 (FIG. 3) and the second waveform 230 (FIG. 4) begins with a common activation sequence 300 shown in FIGS. 3 and 4. In contrast to previously known systems, Applicants have found surprisingly that the activation sequence 300 comprising a plurality of activation cycles 310-1, 310-2, . . . 310-M can be shortened substantially with respect to previously known activation sequences. Each activation cycle 310-n has a first pulse 320 of −1.5 volts for a first interval followed by a more positive second pulse 322 of 0.0 volts for a second interval. The first pulse may have a voltage in a range of approximately −1 volt to approximately −2.5 volts. The second more positive pulse may have a range from approximately −0.2 volt to approximately +0.5 volt. A beneficial effect can be seen from using an activation sequence having as few as two activation cycles (e.g., M=2) wherein each of the two pulses in each cycle has a duration of 100 milliseconds (mS). The number of cycles M may range from 10 cycles to 100 cycles. Optimum results are achieved by an activation sequence that repeats the activation cycle 20 to 40 times (e.g., a range from M=20 to M=40) as illustrated in FIGS. 3 and 4. Repeating the activation cycle 20 times results in an overall duration of the activation sequence of approximately 4 seconds (e.g., 20×2×100 mS=4 seconds). The activation sequence cleans the working electrode through the evolution of hydrogen at −1.5 volts. Coatings (both inorganic and organic) are sloughed off the surface during this step at the selected negative voltage. This method can be used on either platinum or gold working electrodes with a change in the measurement potential.

After the activation sequence 300 is completed, a measurement sequence is applied. As briefly discussed above, the system and method disclosed herein provide two measurement methods. A pulsed amperometric detection (PAD) method is illustrated by the first waveform 220 in FIG. 3. A fixed potential measurement method is illustrated by the second waveform 230 in FIG. 4. The waveform generator 210 is configured to switch modes to either generate the first waveform 220 of FIG. 3 or generate the second waveform 230 of FIG. 4 in accordance with the magnitude of the current to be measured. The waveform generator switches modes in response to a MODE signal from control processor At higher currents (e.g., currents above 500 nanoamperes), the waveform generator 210 generates the waveform 220 of FIG. 3. The waveform of FIG. 3 comprises a pulsed amperometric detection (PAD) method sequence. PAD methods are well known in the art but are not known to have been combined with the above-described activation sequence or to be switchable to a fixed applied measurement potential at low current levels as described below. The measurement potentials and the durations described below are for a gold working electrode. The measurement potentials and the durations can be modified slightly to work with platinum working electrodes.

The PAD measurement sequence 260 represented by the waveform 220 of FIG. 3 comprises a plurality of three-step sequences 400-n (e.g., 400-1, 400-2, . . . 400-N). Each three-step sequence comprises three short pulses at different potentials: a first pulse 410 at a measurement potential E1; a second pulse 412 at a high potential E2; and a third pulse 414 at a negative potential pulse E3. One example of a preferred three-step sequence of pulses comprises:

the first pulse 410 having a duration of approximately 450 milliseconds at 0 volts (E1);
the second pulse 412 having a duration of approximately 200 milliseconds at 800 millivolts (E2); and
the third pulse 414 having a duration of approximately 220 milliseconds at approximately −1.15 volts (E3).

The foregoing PAD sequence is repeated N times wherein N may range from 10 to 40. The current is integrated during each measurement while the E1 potential is applied. The integrated values obtained during the last 4 repetitions are averaged to derive the current which is converted to a value of the water parameter.

In other embodiments, the first pulse E1 in the sequence may have a range of −0.1 volt to +0.3 volt for a duration in a range of 300 to 500 milliseconds; the second pulse E2 may have a range of 0.65 volt to 0.95 volt for a duration in a range of 20 to 300 milliseconds; and the third pulse E3 may have a range of −1.0 volt to −2.5 volts for a period having a range of 20 to 300 milliseconds.

The use of the foregoing switched pulse PAD sequence results in:

(1) Improved calibration stability (requiring less frequent calibration);
(2) Improved accuracy;
(3) Improved precision; and
(4) Faster stability at start up (time to first measurement)

Using the above-described PAD method below signal current magnitudes of 5,000 nanoamperes results in very high standard deviation between measurements reducing resolution and precision. Because of this, the method switches to a fixed potential measurement duration at low signal currents, which is illustrated by the waveform 230 in FIG. 4. The waveform 230 includes the activation sequence 300 as described above with respect to FIG. 3. The activation sequence in FIG. 3 is followed by a measurement sequence 450, which comprises a voltage 452 at a constant fixed potential for a selected duration (e.g., 20 seconds in the illustrated embodiment). The constant fixed potential of the measurement sequence in FIG. 4 is illustrated as 0 volts; however, constant fixed potential can be in a range from approximately −0.05 volt to approximately 0.3 volt. This fixed measurement potential results in a very stable signal corresponding with the chlorine total residual oxidant (TRO) level in both seawater at low concentrations (less than 3 parts per million (ppm)).

In alternative embodiments, the fixed potential measurement may be used for signal current magnitudes below 5,000 nanoamperes. In further alternative embodiments, the fixed potential measurement waveform may be used for signal current magnitudes up to 50,000 nanoamperes.

The method disclosed herein is the first method known to use the combination of:

(1) Fast activation pulses (e.g., having durations of approximately 100 milliseconds);
(2) Activation pulses applied before every measurement in a continuous online measurement system; and
(3) A PAD sequence for higher currents with a switch to a fixed potential at lower currents.

The previous detailed description has been provided for the purposes of illustration and description. Thus, although there have been described particular embodiments of a new and useful invention, it is not intended that such references be construed as limitations upon the scope of this invention except as set forth in the following claims.

We claim:

1. A method for extending the measurement life of a working electrode in a three-electrode amperometric sensor for online measurement of a water parameter, the amperometric sensor including a potentiostat with selectable voltages, wherein the working electrode is a bare electrode, the method comprising:
   selectively switching between a first mode and a second mode, each mode including an activation step followed by a measurement step, wherein:
   the activation step comprises applying a first set of voltages to the working electrode, the first set of voltages comprising a plurality of cycles that switch from a more negative voltage in a range of −1 volt to −2.5 volts to a more positive voltage in a range of −0.2 volt to +0.5 volt, the plurality of cycles ranging from 10 cycles to 100 cycles; and
   in the first mode, the measurement step comprises:
      applying a pulsed amperometric detection (PAD) sequence of three voltages to measure a current corresponding to a level of a water parameter, the sequence of three voltages comprising:
         a first voltage in a range of −0.1 volt to +0.3 volt having a duration in a range of approximately 300 milliseconds to approximately 500 milliseconds;
         a second voltage in a range of 0.65 volt to 0.95 volt having a duration in a range of 20 milliseconds to 300 milliseconds; and
         a third voltage in a range of −1.0 volt to −2.5 volts having a duration in a range of 20 to 300 milliseconds;
      measuring a sensor current through the sensor while the first voltage in the sequence of three voltages is applied;
      repeating the sequence of three voltages for at least 10 times and averaging the sensor currents to derive a current for parameter calculation; and
   in the second mode, the measurement step comprises:
      switching from the PAD sequence of three voltages to a fixed measurement potential to measure the current when the measured current is below a selected signal current value, wherein the fixed measurement potential has a range from −0.05 volt to 0.5 volt and has a duration in a range from 3 seconds to 60 seconds.

2. The method as defined in claim 1, wherein the cycles in the first set of voltages switch from −1.5 volts to 0.0 volts and wherein the plurality of cycles comprises 20 to 40 cycles.

3. The method as defined in claim 1, wherein the cycles in the first set of cycles switch from −1.5 volts to 0.0 volts and wherein the plurality of cycles comprises 30 cycles.

4. The method as defined in claim 1, wherein the first voltage in the sequence of three voltages is 0.0 volts, the second voltage in the sequence of three voltages is 0.8 volt and the third voltage in the sequence of three voltages is −1.15 volts.

5. The method as defined in claim 1, wherein the sequence of three voltages is repeated up to 40 times.

6. The method as defined in claim 1, wherein switching occurs when the selected signal current level is below 50,000 nanoamperes.

7. The method as defined in claim 1, wherein switching occurs when the selected signal current level is below 5,000 nanoamperes.

8. The method as defined in claim 1, wherein switching occurs when the selected signal current level is below 500 nanoamperes.

9. The method as defined in claim 1, wherein the duration is 20 seconds and the measurement potential is 0.0 volts.

10. The method as defined in claim 1, wherein the working electrode comprises gold.

11. An apparatus for measuring a water parameter, the apparatus comprising:
   a three-electrode potentiostat comprising:
   a measurement cell having a working electrode, a reference electrode and a counter electrode; and
   circuitry responsive to an input voltage to generate a current through the measurement cell to cause a voltage between the working electrode and the reference electrode responsive to the input voltage;
   a waveform generator having an output coupled to the potentiostat, the waveform generator generating the input voltage, the waveform generator operating in at least a first mode and a second mode, wherein:
   in the first mode:
      the waveform generator generates the input voltage as an activation sequence followed by a first measurement sequence, wherein:
      the input voltage in the activation sequence comprises a first set of voltages in a plurality of cycles that switch from a more negative voltage in a range of −1 volt to −2.5 volts to a more positive voltage in a range of −0.2 volt to +0.5 volt, the plurality of cycles ranging from 10 cycles to 100 cycles; and
      the input voltage in the measurement sequence comprises a repeated sequence of three voltages comprising:
         a first voltage in a range of −0.1 volt to +0.3 volt having a duration in a range of approximately 300 milliseconds to approximately 500 milliseconds;
         a second voltage in a range of 0.65 volt to 0.95 volt having a duration in a range of 20 milliseconds to 300 milliseconds; and
         a third voltage in a range of −1.0 volt to −2.5 volts having a duration in a range of 20 to 300 milliseconds;
   in the second mode, the waveform generator generates the input voltage as the activation sequence followed by a second measurement sequence, wherein the second measurement sequence comprises a fixed measurement voltage, the fixed measurement voltage having a range from −0.05 volt to 0.5 volt and having a duration in a range from 3 seconds to 60 seconds; and
   a current sensor to sense the current flowing through the measurement cell as a measured current.

12. The apparatus as defined in claim 11, wherein:
   the waveform generator repeats the sequence of three voltages at least 10 times, and
   the measured currents are averaged to derive a current for a water parameter calculation.

13. The apparatus as defined in claim 11, wherein the fixed measurement voltage is 0.0 volts and the duration of the fixed measurement voltage is 20 seconds.

14. The apparatus as defined in claim 11, wherein the working electrode comprises gold.

\* \* \* \* \*